(12) United States Patent
Bauss et al.

(10) Patent No.: US 10,937,532 B2
(45) Date of Patent: Mar. 2, 2021

(54) INFORMATION PROVIDER SYSTEM

(71) Applicant: CAREBAY EUROPE LTD, Sliema (MT)

(72) Inventors: Markus Bauss, Lengdorf (DE); Per Lindstedt, Värmdö (SE); Rasmus Renstad, Stockholm (SE); Nikolaj Hautaviita, Bro (SE); Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 422 days.

(21) Appl. No.: 15/514,717

(22) PCT Filed: Sep. 25, 2015

(86) PCT No.: PCT/EP2015/072137
§ 371 (c)(1),
(2) Date: Mar. 27, 2017

(87) PCT Pub. No.: WO2016/055290
PCT Pub. Date: Apr. 14, 2016

(65) Prior Publication Data
US 2017/0235919 A1    Aug. 17, 2017

Related U.S. Application Data

(60) Provisional application No. 62/060,276, filed on Oct. 6, 2014.

(30) Foreign Application Priority Data

Feb. 23, 2015  (EP) ..................................... 15156116

(51) Int. Cl.
*G16H 20/13*        (2018.01)
*G16H 40/63*        (2018.01)
(Continued)

(52) U.S. Cl.
CPC .......... *G16H 20/13* (2018.01); *A61M 5/2033* (2013.01); *A61M 5/3157* (2013.01);
(Continued)

(58) Field of Classification Search
CPC ............................. A61M 5/3157; G16H 20/13
See application file for complete search history.

(56) References Cited

U.S. PATENT DOCUMENTS 8,355,753 B2    1/2013  Bochenko et al.
2002/0096543 A1  7/2002  Juselius
(Continued)

FOREIGN PATENT DOCUMENTS

EP    2243460 A1    10/2010
TW    200504547 A    2/2005
(Continued)

OTHER PUBLICATIONS

International Search Report and Written Opinion for Int. App. No. PCT/EP2015/072137, dated Apr. 18, 2016.
(Continued)

*Primary Examiner* — Robert A Sorey
*Assistant Examiner* — Kristine K Rapillo
(74) *Attorney, Agent, or Firm* — McDonnell Boehnen Hulbert & Berghoff LLP

(57) ABSTRACT

The present invention relates to an information provider system having a sheet material comprises printed visual information of a product and at least one NFC-tag arranged to said material, wherein said at least one NFC-tag is arranged with a chip containing specific information related to said product and an antenna. At least one switch operably connectable to said NFC-tag is also included such that when said switch is connected to said NFC-tag, an NFC-enabled smart device arranged adjacent said NFC-tag is activated,
(Continued)

whereby said smart device provides further information to a user regarding the specific information of the NFC-tag.

21 Claims, 10 Drawing Sheets

(51) Int. Cl.
| | | |
|---|---|---|
| *G16H 20/17* | (2018.01) | |
| *G16H 20/10* | (2018.01) | |
| *G09B 1/14* | (2006.01) | |
| *G09B 1/32* | (2006.01) | |
| *G09B 5/06* | (2006.01) | |
| *A61M 5/315* | (2006.01) | |
| *A61M 15/00* | (2006.01) | |
| *A61M 5/20* | (2006.01) | |
| *G16H 10/20* | (2018.01) | |

(52) U.S. Cl.
CPC ............... *A61M 15/00* (2013.01); *G09B 1/14* (2013.01); *G09B 1/325* (2013.01); *G09B 5/062* (2013.01); *G09B 5/065* (2013.01); *G16H 20/10* (2018.01); *G16H 20/17* (2018.01); *G16H 40/63* (2018.01); *A61M 2005/202* (2013.01); *A61M 2005/2013* (2013.01); *A61M 2205/3569* (2013.01); *A61M 2205/3584* (2013.01); *A61M 2205/581* (2013.01); *A61M 2205/582* (2013.01); *A61M 2205/583* (2013.01); *A61M 2205/60* (2013.01); *A61M 2205/6009* (2013.01); *A61M 2205/609* (2013.01); *A61M 2205/6054* (2013.01); *G16H 10/20* (2018.01)

(56) References Cited

U.S. PATENT DOCUMENTS

| | | |
|---|---|---|
| 2004/0178112 A1 | 9/2004 | Snyder |
| 2005/0182358 A1 | 8/2005 | Veit et al. |
| 2005/0241983 A1 | 11/2005 | Snyder et al. |
| 2006/0169773 A1 | 8/2006 | Lyons et al. |
| 2007/0129708 A1 | 6/2007 | Edwards et al. |
| 2011/0040757 A1* | 2/2011 | Kossi ..................... G06F 16/41 707/737 |
| 2011/0111794 A1 | 5/2011 | Bochenko et al. |
| 2011/0231204 A1* | 9/2011 | De La Huerga ....... G16H 10/65 705/2 |
| 2012/0326885 A1 | 12/2012 | McCarty |
| 2013/0046197 A1 | 2/2013 | Dlugos, Jr. et al. |
| 2013/0181814 A1 | 7/2013 | Smith |
| 2013/0184649 A1 | 7/2013 | Edwards et al. |
| 2013/0285681 A1 | 10/2013 | Wilson et al. |
| 2014/0292493 A1 | 10/2014 | Clarke et al. |
| 2014/0312074 A1 | 10/2014 | Madsen et al. |
| 2015/0025498 A1* | 1/2015 | Estes ..................... G16H 40/63 604/506 |

FOREIGN PATENT DOCUMENTS

| | | |
|---|---|---|
| TW | 200706180 A | 2/2007 |
| TW | 201212888 A | 4/2012 |
| TW | 201406420 A | 2/2014 |
| WO | 2004/023245 A2 | 3/2004 |
| WO | 2004/084116 A1 | 9/2004 |
| WO | 2006/083933 A1 | 8/2006 |
| WO | 2012/108938 A1 | 8/2012 |
| WO | 2013/167701 A1 | 11/2013 |

OTHER PUBLICATIONS

European Search Report for EP Application No. EP 19173236, dated Aug. 9, 2019.

* cited by examiner

INFORMATION PROVIDER SYSTEM

CROSS REFERENCE TO RELATED APPLICATIONS

The present application is a U.S. National Phase Application pursuant to 35 U.S.C. § 371 of International Application No. PCT/EP2015/072137 filed Sep. 25, 2015, which claims priority to U.S. Provisional Patent Application No. 62/060,276 filed Oct. 6, 2014 and European Patent Application No. 15156116.4, filed Feb. 23, 2015. The entire disclosure contents of these applications are herewith incorporated by reference into the present application.

TECHNICAL FIELD

The present invention relates to an information provider system and in particular an information provider system having a user interaction interface and RFID-technology for providing specific information.

BACKGROUND

Medicament delivery devices for self-administration have been on the market for a number of years. In order for the devices to be handled by non-professionals, they have to be easy to use and intuitive. In order to "teach" the users on how to handle the devices, user instructions or user manuals have been developed that instruct the user step by step how to handle the device from initiation to either discarding or reloading the device. Further, since many of the drugs are vital or at least very important to the patient there is a desire from physicians and other professionals to obtain information that the patients medicate according to prescribed schemes. The desired information could include the type of drug, delivery times and dates, and dose size. Additional information that could be beneficial to the physician is that the correct drug administration procedure has been observed; that the drug has the prescribed temperature during drug delivery; that the right injection depth has been attained and that the correct injection speed has been used, when the medicament delivery device is an injector. In general, there is an increased demand for information regarding user adherence.

For some medicaments the primary package has been used to provide information regarding user adherence, i.e. the package has obtained a "smart" function in addition to being merely protective. For instance the company MWV has developed a smart package "Cerepak". The package comprises a microprocessor embedded into the package material and circuits of conductive ink. When a tablet is removed, a signal is generated that is transmitted to the microprocessor, it is designed to record and store the date, time and location for each taken pill. The information stored can further be up-loaded by a smart device where RFID-technology (radio frequency identification) may be utilized. One advantage with RFID is that passive RFID-tags do not require a battery. The tags can therefore be made very small. In addition, the package may be supplied with a questionnaire having push-buttons with conductive ink where the user can answer questions regarding Quality of Life.

Even though the "Cerepak" package is intelligent in the sense that it may record and store information regarding patient adherence, the full potential is not employed in that information, or data, is only transmitted one-way, from the smart device to suitable receivers in data networks. There is thus room for improvements in this area.

Also, studies have shown that using pictographic instructions in conjunction with written and oral instructions increases patient comprehension. In addition, there is currently some data suggesting that although some pictograms are universal, others may have some cultural specificity. For many users, local languages must be used as much as possible to maximize the benefits of the written and visual health information. Pictograms give health professionals a means of communicating medication instructions to people who do not share their language and/or who may be illiterate. Pictograms may also be used for those who have a slight cognitive impairment or difficulties seeing, such as the elderly. In addition, time to educate patients how to use a medicament and/or a medicament delivery device is often brief or non-existent. Far too often this is a waste of time and money, but moreover, improper technique of using a medicament and/or a medicament delivery device leads to e.g. poor absorption of the medications. Not all individuals can effectively understand and learn from written materials, and other methods are used to help such as pictograms, leaflets, or videos. Pictorial representations have been shown to improve recall of medical instructions in a clinical setting and pictograms have been shown to be an effective tool as well, enhancing consultations and aiding understanding. Moreover, videos trump them all. Video tutorials are the best option for high-quality, consistent and repeatable patient instruction and furthermore, a cost-effective and efficient method of providing basic information to patients about a disease and its treatment, and medical instructions.

Instructions may nowadays be stored in a smart device or retrieved by a smart device, however, elderly and some people are not so confident with the smart device's technology and then it would be an improvement to have an easy user interface that effectively facilitates how to retrieve the instructions.

SUMMARY

The aim of the present invention is to provide an information provider system that is simple, reliable, low-cost, that can be used with conventional smart devices common on the market and used by a majority of patients that handle medicament delivery devices for self-administration.

This aim is solved by a system comprising the features of the independent patent claim. Preferable embodiments of the invention form the subject of the dependent patent claims.

According to an aspect of the invention, it comprises an information provider system, preferably for a medicament delivery device. The information provider system comprises a sheet material, preferably foldable sheet material. The sheet material may preferably be arranged with printed information such as for example visual information of a product or products. The information provider system may further be arranged with at least one NFC-tag arranged to the material. The NFC-tag may in this respect be attached as a label on the sheet material or be embedded in the sheet material.

The at least one NFC-tag is preferably arranged with a chip containing specific information related to the product, and an antenna. Further at least one switch may be operably connectable to said NFC-tag. The switch may be connected to the NFC-tag by a manual operation causing an NFC-enabled smart device arranged adjacent said NFC-tag to be activated, whereby the smart device may provide further information to a user regarding the specific information of the NFC-tag.

Thus the information provider system is not active until the switch is manually operated. Then the specific information on the NFC-tag is used to obtain further information via the smart device, which is presented to the user handling the smart device.

The further information regarding said specific information may be stored in the smart device, but the smart device may also be arranged with communication systems capable of communicating with remote databases, wherein the further information regarding said specific information is retrieved from said remote databases. Thus the further information presented to the user may either come directly from the smart device when stored therein, or be downloaded from remote databases. In this regard, the downloaded further information may also be stored in the smart device for subsequent use. It is to be understood that the further information may be provided visually and/or audibly, i.e. further information may be presented on a display of the smart device and/or transmitted from its loudspeakers, e.g. pictograms, audio files and/or videos.

According to one feasible solution, the at least one switch may be positioned between the chip and the antenna, whereby the antenna is connected to the chip when the switch is operated. With this solution, the NFC-tag cannot receive any power from an NFC-enabled smart device placed adjacent the antenna until the switch is operated and the antenna is connected to the chip. It is only then that the antenna may draw power from the smart device and activate the NFC-chip to transmit specific information to the smart device, whereby the smart device presents further information.

In connection with this solution, the smart device may be arranged to register repeated operations of the at least one switch such that the smart device may provide new further information to a user regarding the specific information each time the at least one switch is operated. With this solution, only one NFC-chip and one switch may be used for presenting a plurality of further information, such as e.g. a step-by-step user instruction.

According to another solution, the information provider system may comprise a plurality of switches operably connected to the NFC-tag, and wherein the smart device is arranged to register operations of specific switches of the plurality of switches such that the smart device provides further information to a user regarding the specific information when a specific switch is operated. With a plurality of switches, the information provider system can be used to present a plurality of further information via the smart device.

In order to handle a plurality of switches, it is advantageous if the information provider system further comprises a microcontroller operably connected between the plurality of switches and the NFC-tag, for handling the plurality of input signals from the plurality of switches.

Preferably the specific information is related to a product such as e.g. a medicament delivery device. When a plurality of switches is used, the presentation on the sheet material may comprise a plurality of products, wherein the plurality of switches may be associated with the plurality of products, respectively.

According to a favourable solution, the sheet material may comprise a packaging for a product and wherein the printed visual information presented on the packaging and the specific information in the chip is related to the product, and wherein the product to be contained in the packaging is a medicament delivery device. In that respect the further information provided to a user by the smart device comprises user instructions of the medicament delivery device, and/or information about the medicament. Further, the user instructions may be designed as step-by-step handling instructions that are changed each time a switch is operated. As an alternative, the user instructions may be changed when one of the plurality of switches is operated, and/or the user instructions may be changed when a combination of switches is operated.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 1 displays a first scenario according to the invention comprising an NFC-tag and a smart device, FIG. 2 displays the use of a label comprising an NFC-tag capable of providing status information of several features and functions of a medicament delivery device, FIG. 3 displays a second scenario according to the invention with a higher level of integration between NFC-tags and smart devices, FIG. 4 displays an example of the use of several NFC-tags in one medicament delivery device, FIG. 5 displays an example of physical integration of a medicament delivery device comprising NFC-tags and a smart device, FIG. 6 displays schematically an information provider system, FIG. 7 displays a first embodiment of an information providing function that may be used in the information providing system of FIG. 6, FIG. 8 displays a second embodiment of an information providing function, FIG. 9 displays an information provider system as a package for a product, and FIG. 10 displays the use of the information provider system of FIG. 9.

DETAILED DESCRIPTION

Figure 1:
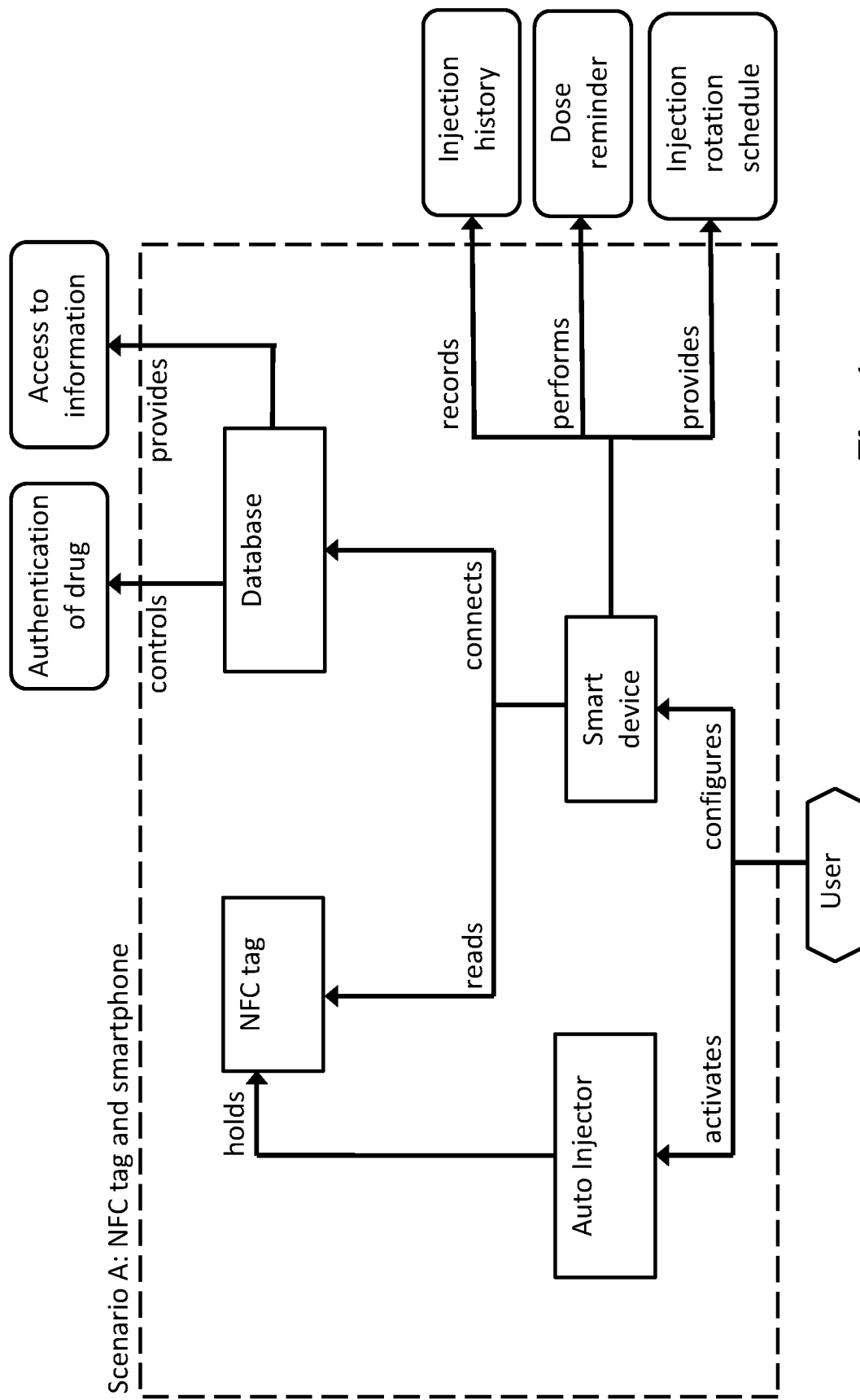

In the following description, the wording smart devices will be used. In this context, smart devices may include electronic devices that are provided with processors that are capable of running computer programs as well as storage space to store programs as well as data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further the smart devices may be provided with antennas for wireless communication with the networks. Also, the smart devices may be arranged with receiving and transmitting mechanisms capable of communicating with NFC tags as well as programs capable of establishing and handling the communication with the NFC tags.

Further, in the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, dispensers for medicament in tablet form. The medicament delivery devices may be of either disposable type or re-usable type and may be provided with medicament containers suitably arranged for specific drugs in specific forms.

The communication system of the present application comprises the use of radio frequency identification technology, RFID. In particular, high frequency RFID provides a number of advantages regarding communication. The possibilities of using HF RFID are numerous and in particular provides the use of Near Field Communication, NFC. NFC is particularly suitable because it is a set of standards for smartphones and the like smart devices to establish radio communication. NFC is a set of short-range wireless technologies, typically requiring a distance of 10 cm or less. NFC operates at 13.56 MHz on ISO/IEC 18000-3 air interface and at rates ranging from 106 kbit/s to 424 kbit/s. NFC always involves an initiator and a target; the initiator actively generates an RF field that can power a passive target. This enables NFC targets to take very simple form factors such as tags, stickers, key fobs, or cards that do not require batteries.

In the following description of the technology used the word NFC-tag will be used. In this context it is to be understood that NFC-tag will comprise an NFC-chip connected to a circuit as well as an antenna. NFC-tag is not limited to be integrated in a patch or label, but may be a stand-alone unit, or integrated in the material used for manufacturing medicament delivery devices. Further, the NFC-tag may include further features and components that are needed for the required or desired purposes and applications as will be apparent below.

NFC tags contain data and are typically read-only, but may be rewriteable. They can be custom-encoded by their manufacturers or use the specifications provided by the NFC Forum, an industry association charged with promoting the technology and setting key standards. The tags can securely store personal data such as debit and credit card information, loyalty program data, PINs and networking contacts, among other information.

Near-field communication uses magnetic induction between two loop antennas located within each other's near field, effectively forming an air-core transformer. There are two communication modes, passive and active mode. In the passive communication mode, the initiator device provides a carrier field and the target device answers by modulating the existing field. In this mode, the target device may draw its operating power from the initiator-provided electromagnetic field, thus making the target device a transponder. In the active communication mode, both initiator and target device communicate by alternately generating their own fields. A device deactivates its RF field while it is waiting for data. In this mode, both devices typically have power supplies. As to be understood in the following description in the area of medicament delivery devices, the initiator device is a smart device as defined above, and the target device is a medicament delivery device as defined above.

Regarding medicament delivery devices, they can be arranged with NFC tags in order to perform a number of tasks. The NFC tags may be arranged as labels on an outer or inner surface of a housing of a medicament delivery device. It may also be embedded or cast into the material of the medicament delivery device.

FIG. 1 displays a first possible scenario comprising NFC tags and smart devices. In its most simple application, the NFC tags may be arranged to perform functions that do not require specific approvals from national drug regulation authorities such as the FDA in USA that the device is e.g. safe and effective. Such functions may comprise authentication of the drug that is inside the medicament delivery device. In that respect, the NFC tags may be placed on the medicament containers, for example if the medicament delivery device is a reusable device that may be used for a number of medicament containers.

Alternatively the NFC tags may be a part of the medicament delivery device, either as a label added to the device during assembly or embedded into the material when casting the device, e.g. in the housing.

The NFC tags may further provide information regarding expiry date of the drug. Alternatively, the communication with the smart device may trigger the smart device to connect to a remote database where information regarding the drug may be retrieved, such as the expiry date. The information from the database may further include if any recalls can or have affected the unique drug and/or the medicament delivery device.

The NFC tags may further include functions that, when communicating with the smart device, may start programs or applications in the smart device that provides the user with information. The programs and/or applications may be stored in the smart device but may also, or instead, be stored in external databases that are either retrieved by the smart device or run via web browsers. In that respect, the NFC tags may trigger a web browser of the smart device to activate certain URL's. These may comprise e.g. instructions for use of the medicament delivery device, where the URL may lead to a web page containing a written description of how to use the device.

In addition, or instead, the targeted web page may include a video recording, that also could include a narrator, showing and describing how to use the device. Further information that could be provided to the user is contact information to health care providers, such as e.g. telephone numbers, e-mail addresses, maps etc. Further information to a user may comprise reminders and schedules for dose delivery, such as dose delivery intervals, at what times during the day the dose should be taken etc. This dose delivery information may be manually generated in that the user or a physician enters the information into the smart device, which could be done via a calendar function. The information could also be generated electronically from prescription, wherein the information is obtained through communication with external databases via networks. The smart device could then provide the user with reminding information when it is time to take a dose of medicament, wherein the reminder could include all sorts indications such as text messages on the display of the smart device, audible signals or voice messages, vibrations, flashes, just to mention a few possibilities.

Other types of information could comprise reminders and schedules regarding using different dose delivery sites, which may be quite important when injection devices are used and wherein repeated injections on the same site may cause scars tissue, and or where the drug injected may cause irritation of the skin. These schedules could comprise visual information on the display of the smart device showing graphically where on the body the next dose should be delivered. This type of information may then be displayed in connection with the reminder of taking a dose of medicament.

The storage facilities of the smart device may further be used to store unique ID of the drug used, wherein specific information may be connected to the drug in order to build up medicament delivery history. In this respect, medicament delivery history, e.g. injection history, may comprise information regarding date and time of information read by the smart device of performed drug delivery occasions. It is in this scenario thus important that the reading of the NFC-chip is performed close after the dose has been delivered in order for the information to be as accurate as possible.

The information may further, or instead, comprise delivered dose size, if for example the medicament delivery device may be provided with mechanism for setting and delivering different dose sizes. The information may be compared by the smart device with prescribed drug delivery intervals and/or dose sizes in order to detect any deviations. Any deviations may be stored in the smart device and/or transmitted to the physician of the user. It is however to be understood, as mentioned above, that the information, written and/or visual and/or audible, may be comprised in the programs or the applications that may be stored in the smart device. The user may also be alerted by the smart device of any deviations and may possibly be given options regarding remedy of the deviations.

Figure 2:
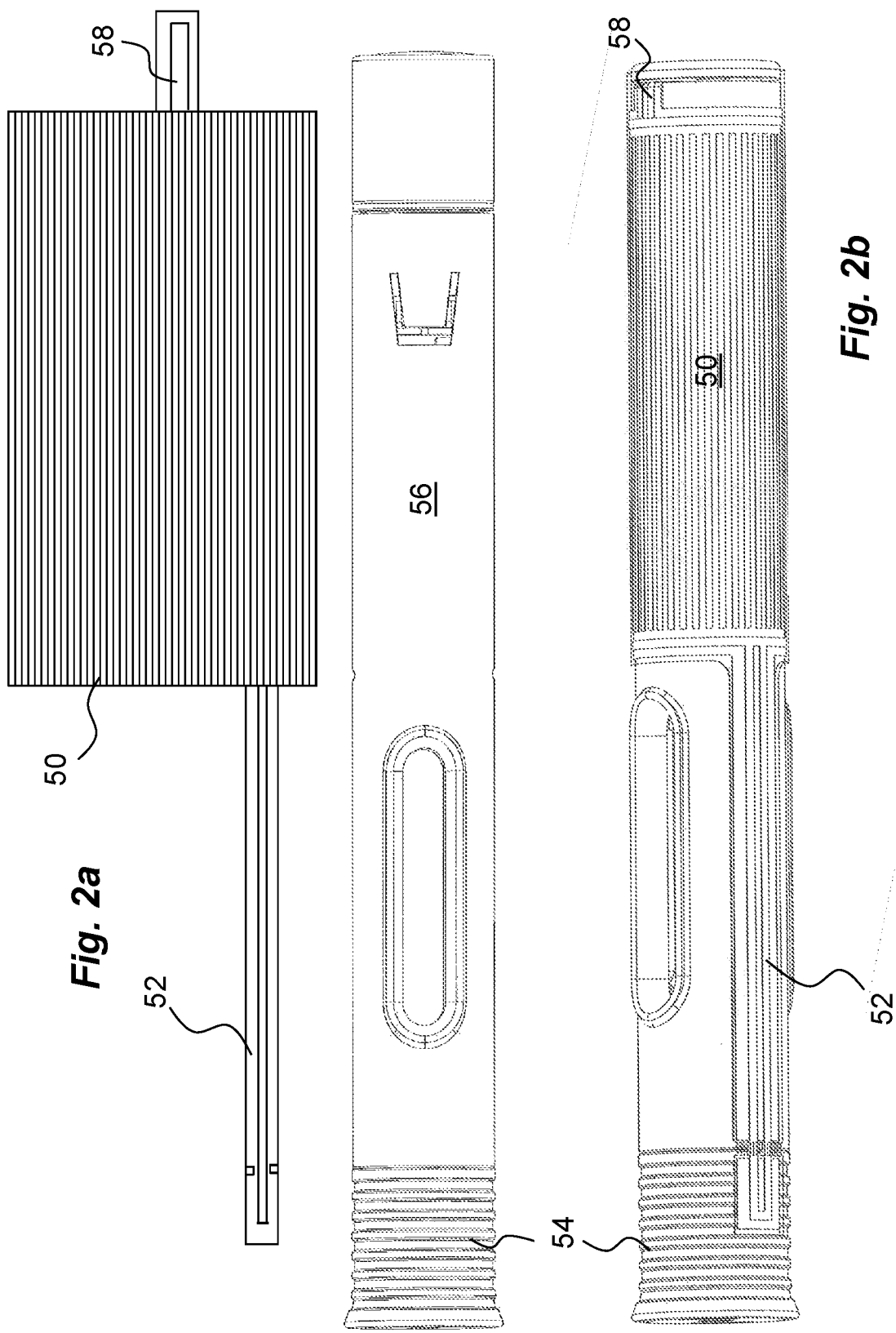

A further scenario regarding the present invention is to provide more information regarding the status of the medicament delivery device in the communication between one or more NFC chips and smart devices, thereby increasing the level of integration between the medicament delivery device and the smart device. An example of this is shown in FIG. 2. In this scenario, NFC-chips 50 are used that are capable of detecting and identifying if a certain circuit on the medicament delivery device 56 is open or closed. This capability may be used for providing information regarding the status of the medicament delivery device 56.

Figure 3:
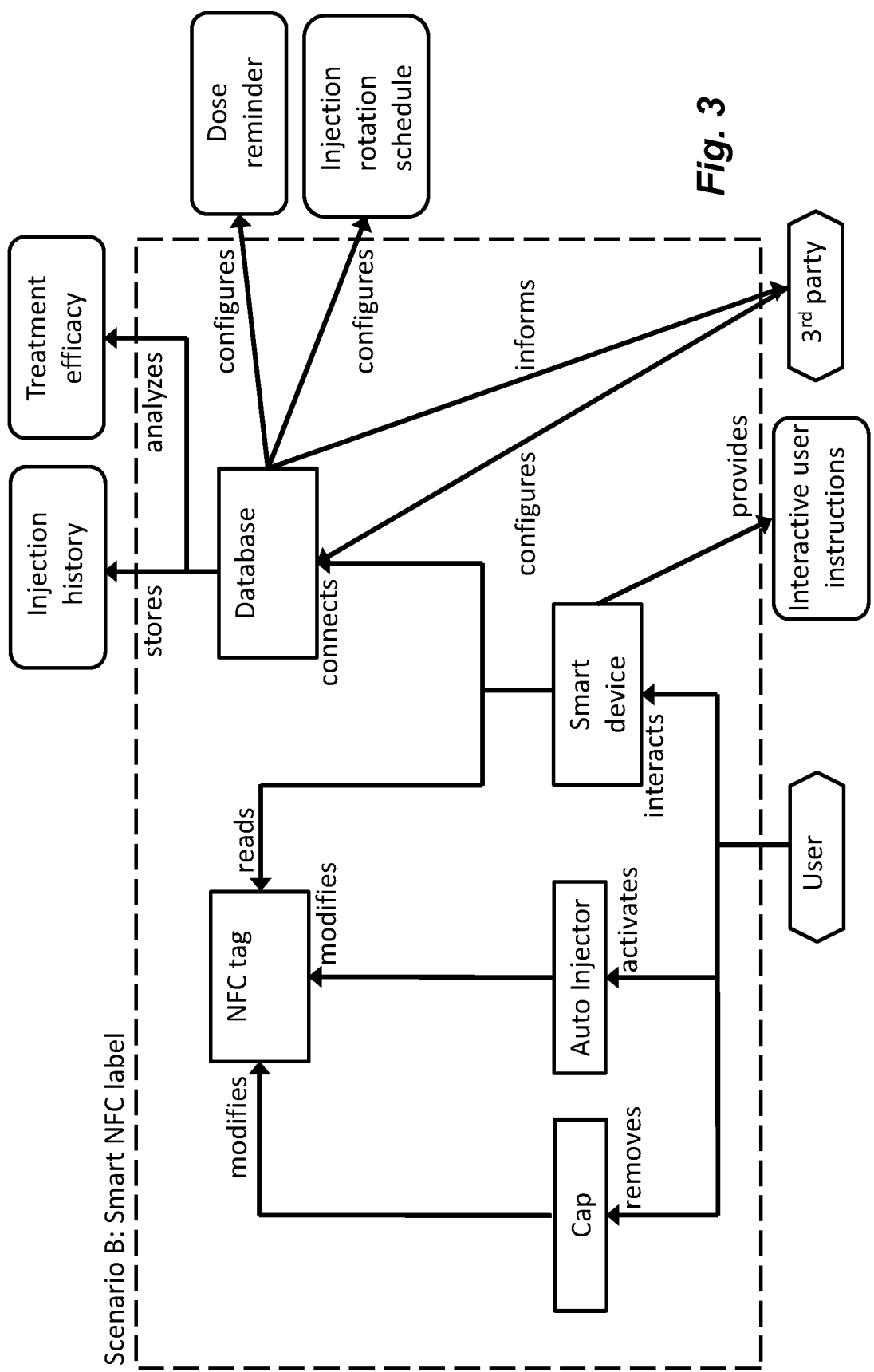

For instance circuits may be connected to a number of functions and components of the device. As an example, a circuit 52 may be connected to a protective cap 54 of the device. When a user removes the cap 54 the circuit is broken and thus closed, which may be detected by the NFC 50 and this information may be transmitted to the smart device as seen in FIG. 3. The smart device can store this information and/or transmit it to external databases, adding to the device history, which may be monitored by e.g. the physician of the user.

Circuits may thus be connected to a number of components for providing status information. Such status information may comprise end of dose delivery. It may for example be important for a user to know when an injection sequence has ended and that it is safe to remove the device from the injection site. In this case a circuit 58 may be affected by moving components at the end of dose delivery, wherein the circuit acts as a switch, e.g. from open to closed. For instance, the moving component may be a force member like a drive spring that is capable of acting in the distal direction of the medicament delivery device at the end of an injection sequence, wherein the distal action will affect the NFC circuit 58. The switch information detected by the NFC is transmitted to the smart device, wherein the smart device is arranged to indicate to the user that the device may safely be removed. Also, this information confirms that the device is used.

The circuits and switches may further be used as interactive, step by step, instructions. For example, the smart device may be provided with an instruction application showing a user in a step-wise manner how a device should be handled. When one step has been performed, whereby a certain circuit has been affected and detected by the NFC and transmitted to the smart device, an OK or positive response is provided by the smart device and displayed to the user. The instruction application then shows the subsequent handling step to be taken. In this manner, all steps affect different circuits that in turn provide the NFC chip with status information. This status information is successively transmitted to the smart device and appropriate information is displayed to the user by the instruction application.

In this context it is to be understood that there are numerous functions that can be monitored by the use of circuits connected to the NFC chips. These could include tamper evidence of the medicament delivery device, tamper evidence of trying to manipulate e.g. a label comprising an NFC attached to a medicament delivery device.

In connection with the increased integration of the medicament delivery device and the smart device, further information could be collected in order to increase the understanding of the effects of a certain treatment scheme, e.g. disease monitoring. The programs or applications that are used in the smart device in connection with the medicament delivery devices may further include questionnaires that are filled in by the user in connection with a dose delivery operation. The questionnaire may include a number of questions regarding the current status of the patient and may preferably be configurable depending on therapy, disease and user needs. The areas that might be handled may include quality of life, cognitive function, pain, fatigue, nausea, mental health, etc. The answers of the questionnaire may then be transmitted from the smart device to external databases together with information collected via the NFC-tags for processing and evaluation to find positive or negative correlations between the treatment scheme and type of medicament in relation to the perceived condition of the patient.

Figure 4A:
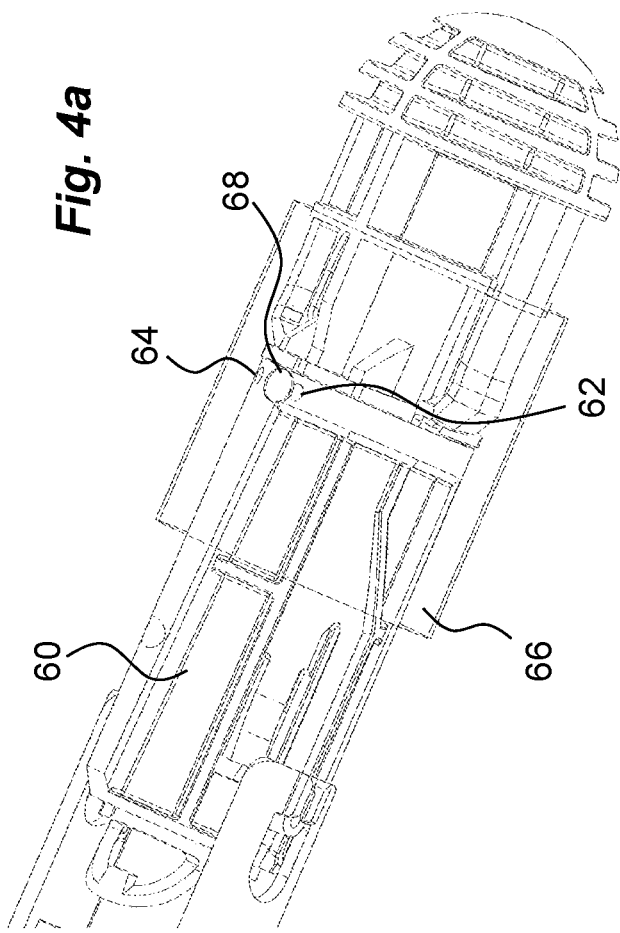
Figure 4B:
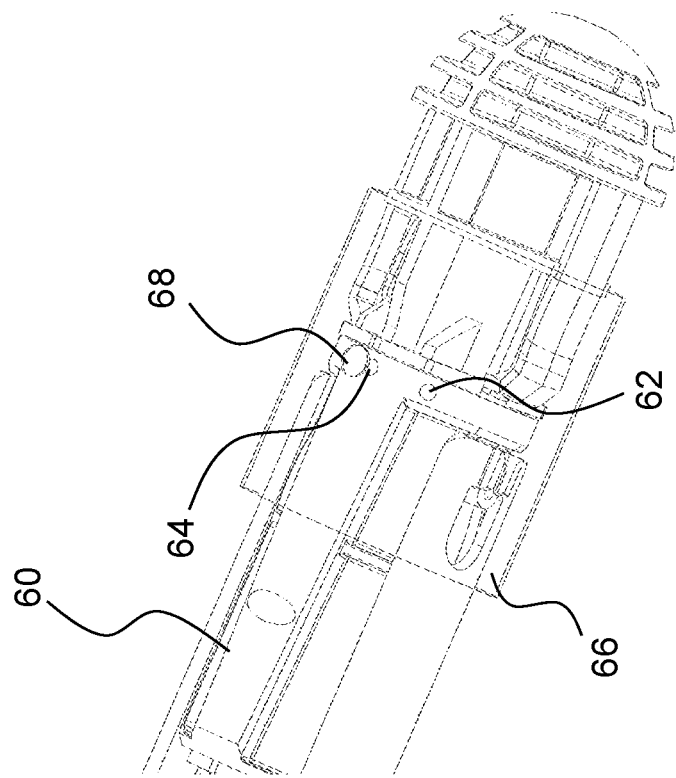

It is to be understood that more than one NFC-tag may be used on one device, where the different NFC-chips are arranged to handle for example different states of a device. In this scenario it may be important that only one NFC-tag at the time may be read by the smart device. FIG. 4 shows a possible use of several NFC-tags. Here the medicament delivery device is arranged with a component 60 that is rotatable inside the housing of the device and is provided with two NFC tags 62, 64. Before dose delivery the component 60 has one rotational position, FIG. 4a, and after completed dose delivery, the component 60 has a second rotational position, FIG. 4b. This fact may be used in that each position provides information from separate NFC-tags. In order to ascertain that only one NFC-tag at the time can be read, a metallic layer 66 is attached to the housing in the area of the NFC-tags, where the metallic layer 66 acts as a shield, blocking reading of the NFC-tags 62, 64. The metallic layer 66 is further arranged with an opening 68, which opening 68 is positioned in relation to the NFC-tags that a first NFC-tag 62 is aligned with the opening 68 at the first position of the rotatable component, FIG. 4a, and that a second NFC-tag 64 is aligned with the opening 68 in the second position, FIG. 4b.

Thus, in the first position, FIG. 4a, before being used, the first NFC-tag 62 may be read by a smart device, providing information that the device is unused. Further, in the second position, FIG. 4b, after use, the second NFC-tag 64 may be read by a smart device, providing information that the device has been used. It is to be understood that further NFC-tags may be used, for instance as described above in connection with removal of a protective cap. There are numerous ways in which the functions may be physically implemented. For instance, the several NFC-tags may be integrated into the material when the rotatable component is manufactured, e.g. moulded in plastic. The NFC-tags may also be attached onto the surface of the rotatable component, either glued directly or being integrated in a label that is attached to the rotatable component. Also the metallic layer may be formed in different ways. It may also be integrated in the material of the housing or be arranged as a label that is attached on the inner or outer surface of the housing.

Figure 5:
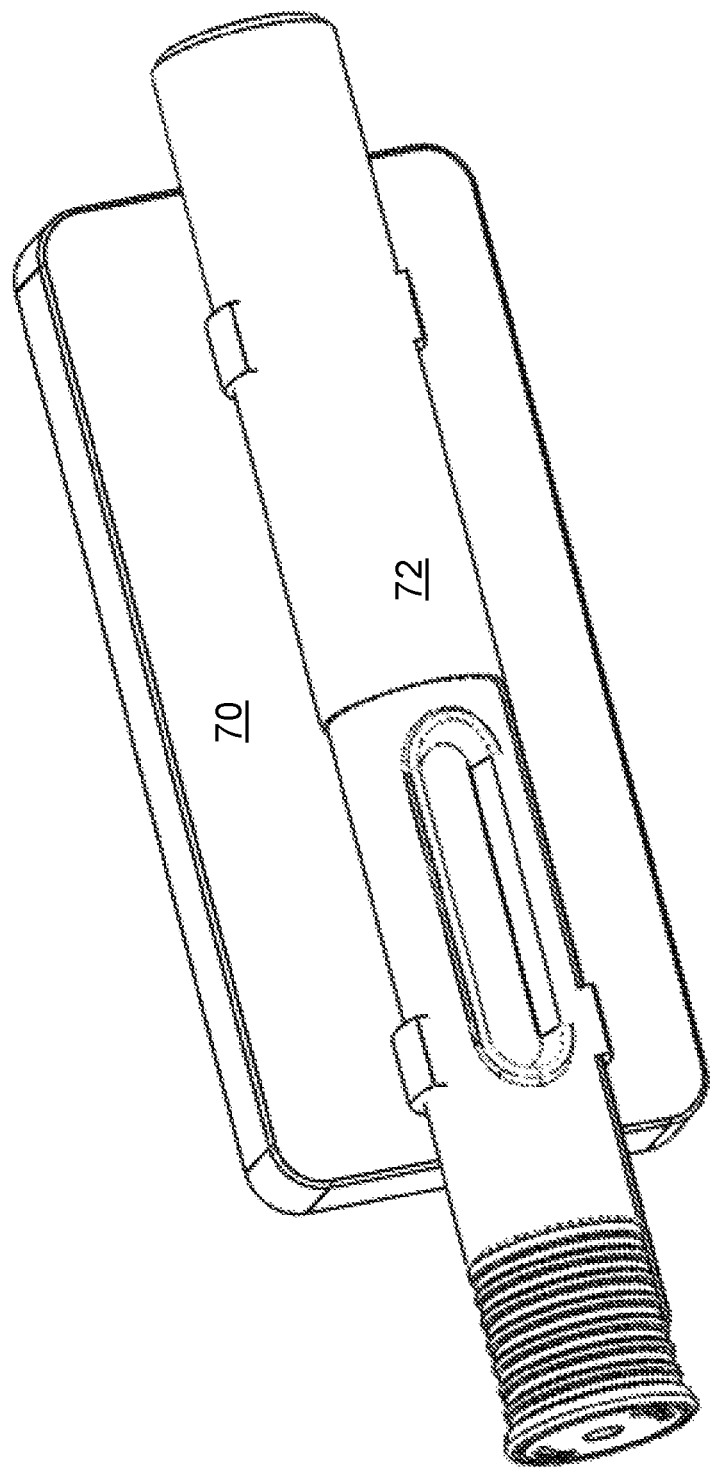

According to a further scenario of the present invention, an attachment 70 could be provided to the smart device, FIG. 5. The attachment could for example comprise a shell enclosing at least part of the smart device. This attachment enables a number of features and functions.

Preferably the attachment 70 is arranged to accommodate or hold a medicament delivery device 72. It is even feasible that the attachment and the medicament delivery device are integrated into one unit. With this feature, an even closer integration between the medicament delivery device and the smart device is obtained. This in turn provides additional advantages and features. One advantage is that the fixed connection between the medicament delivery device and the smart device enables correct reading position of the NFC-tag. Thus, the user does not have to try different distances between the medicament delivery device and the smart device in order to obtain information from the NFC-tag.

Further, if the smart device is not equipped with an NFC-reader, the attachment 70 could be provided with such an NFC-reader, thereby adding functionality to the smart device. The integration of the medicament delivery device and the smart device further provides real time interactive user instructions as well as correct injection times, dates and dose quantities because of the close connection between the medicament delivery device and the smart device because of real time reading of the NFC-tag. The injection times, dates and dose quantities can be recorded directly in the smart device for further processing or transmittal.

Many smart devices are arranged with motion sensors in three dimensions, which functionality could be used in connection with handling of the medicament delivery device. For instance, the smart device could detect how it, and thus the medicament delivery device, is being held. This may be important for some types of drugs and for some types of medicament delivery devices in that the medicament delivery device has to be held in a certain way during some steps when used. This could for example be a medicament delivery device using a so called dual chamber medicament container, where it can be important how the medicament container is held during mixing and priming. The motion sensors of the smart device could then be used to detect how the medicament delivery device is held and could inform a user on how to hold the device and alert the user if the device is not held according to instructions.

Further features of the smart device that could be used with the integrated medicament delivery device include the use of a camera that is often an integrated part of the smart device. The camera could then be used to take photographs of the content of the medicament container, which often is transparent, in order to obtain information regarding the status of the drug. For example, colouring or opacity of a drug may indicate that something adverse has happened to the drug, such as exposure to temperatures outside the prescribed range, such that the drug should not be used. The comparison of colour or opacity may be performed directly by the user in an application in the smart device, or the picture may be sent by the smart device to an external site where skilled personnel perform the comparison and alert the patient of any deficiencies of the drug and advice as to how proceed.

Regarding adherence and patient responsibility, there are features and functions of the smart device that may be utilized. Some drugs and treatment schemes are very expensive to the national healthcare authorities and a lot of responsibility is put on the users to really adhere to the treatment schemes. There has been discussions in several countries in the world that if patients do not adhere to an expensive treatment, they should be forced to pay for the continued treatment, fully or partly, the arguments being that those persons that are not interested enough in a treatment should have to pay for it. The information and drug delivery history obtained from the NFC-tags could be used to monitor the adherence.

In that respect, biometrical sensors such as fingerprint sensors, eye and/or face recognition via cameras on the smart devices mat provide proof of a user of a certain medicament delivery device, providing proof that it is the legitimate user that has activated the medicament delivery device for delivering a dose. Biometrical sensors may further be used in order to ascertain that the device cannot be accidentally, or wilfully, used by a third person.

The functionality of the NFC-tags may be further enhanced by adding a battery in that a timestamp of activation is achievable. For instance, when a switch as described above is affected, such as closing a circuit, a power circuit from the battery is activated. An internal clock in the NFC-chip is thereby activated, starting to count elapsed time. This time information is then transmitted to the smart device, which could be used for a number of functions. For instance, if the clock is activated by an end of dose delivery sequence, then the smart device can easily calculate when a subsequent dose delivery is due according to dose delivery schemes contained in e.g. applications in the smart device. The smart device could then generate reminders to a user until the smart device has read information from another NFC-tag that a subsequent dose has been delivered.

Additional functionality when using a battery is that correct time information of a performed function of the medicament delivery device, such as dose delivery, is obtained regardless of when the information is read from the NFC-tag. Further, when monitoring users of a medicament delivery device during clinical trials, the feature could be used as a hidden stamp of e.g. injected dose. Used devices are then collected by the organiser of the clinical tests and actual times as read from the NFC-tags are compared with the times stated by the users in their handling notes.

One type of battery that could be used is a small one, such as a thin printed battery or a small button cell. For the above purposes there is a low capacity requirement since the battery is activated only when needed and is only used for powering the internal clock, thus there is no standby consumption. However, it is of course possible to use larger batteries in connection with NFC-tags, which enables further features and functions.

For example, if a larger battery is used, the NFC-tag could use the temperature sensor that is built into the NFC-chip. This may be an advantage because then the temperature of a medicament delivery device and/or a medicament container may be monitored and logged for instance during transport. This might be important for a number of drugs that are temperature sensitive, whereby it can be ensured that the quality of the drug has not been affected by temperature variations outside approved ranges. Also, the temperature sensor could be used to provide information when a drug has reached a target temperature for delivery. The information is then communicated to the smart device, where the latter provides handling and temperature information to the user.

When a larger battery is used, the NFC-tag could be arranged with LED's of different colour, or one LED that can change colour. The LED's are then connected to the NFC-tag such that when the temperature sensor senses a certain temperature, a certain colour is lit. When the temperature changes above or below a threshold, another colour is lit. For example, if the temperature of a drug is above or below a permissible drug delivery temperature range, then one colour is lit, e.g. a red light, indicating that the drug cannot be used yet. When then the temperature reaches the permissible range, e.g. room temperature, then the light is changed to e.g. green, indicating that the drug now may be used.

Furthermore, the temperature sensor of the NFC-chip may be used to indicate when medicament container has been emptied, i.e. a dose delivery has ended. If the NFC-tag is placed properly in relation to the medicament container, the temperature sensor may sense the temperature change that occurs between the temperature of the drug and the temperature of the empty medicament container. This significant temperature change may be used to trigger information to the smart device that the dose delivery had ended and that it is safe to remove the device. Also here, when a larger battery is arranged, there is enough power to drive for instance a light source, a vibrator and/or a summer connected to the NFC-circuit, in order to provide visual, tactile and/or audible information that a dose has been delivered.

There are further areas where NFC-tags could be used together with smart devices in medicament delivery device applications. For tutorial purposes, for instance for first time users, a sheet material could be used as an information provider, where the sheet material could be in the form of packaging of a medicament delivery device. The information provider may then be used for tutorial purposes as well as for installing specific programs and applications in a smart device, which programs and applications are to be used together with the medicament delivery device.

Figure 6:
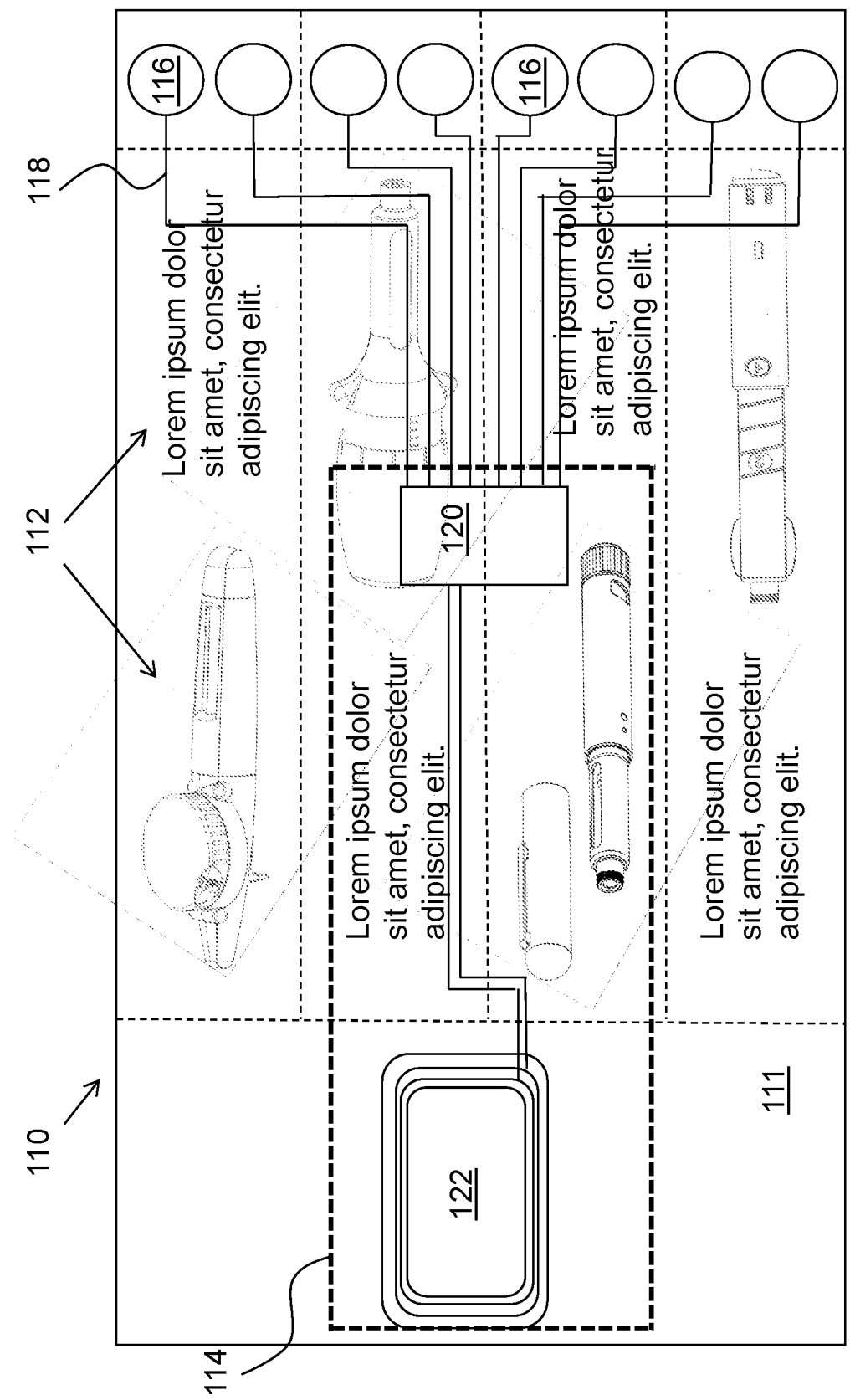

FIG. 6 shows a general example of an information provider system 110. It comprises a sheet material that preferably is foldable. The sheet material 111 may be layers of paper, cardboard, plastic or combinations thereof. The information provider system 110 may further be arranged with printed visual information 112 on one or both sides of the sheet material 111. The printed visual information 112 may comprise any suitable content that a producer of the information provider system may want to communicate. It could for example be a product presentation, where both text and figures/pictures may be shown.

In order to increase the functionality of the information provider system, an NFC-tag 114 may be included. The NFC-tag 114 could for example be arranged on a label having an adhesive on one side. The label is then attached with its adhesive side against one side of the material of the information provider system. As an alternative, the NFC-tag 114 could be embedded in the material when the material is manufactured. When the information provider system 110 is made of several layers of material, an embedded solution is especially advantageous. Further, the information provider system 110 comprises a number of specific contact areas, e.g. printed button areas that are intended to be touched or contacted by a user. Each specific contact area comprises some sort of switch 116 or activator that is affected when the specific area is touched. The switch 116 could be a simple breaker having two end leads that are brought together when the specific contact area is pressed. The switches 116 are connected to an NFC-chip 120 of the NFC-tag 114 via suitable circuitry 118. For instance the circuitry could be created by conductive ink. The NFC-tag 114 further comprises an antenna 122 that may also be embedded in the material of the packaging and connected to the NFC-chip 120. The NFC-tag 114 is arranged to cooperate with an NFC-enabled smart device 124 via the antenna 122 when in communication range.

In that respect, the information provider system 110 may comprise a marked area for placing the smart device, wherein the marked area is positioned in relation to the NFC antenna 122 such that a good connection may be established.

Figure 7:
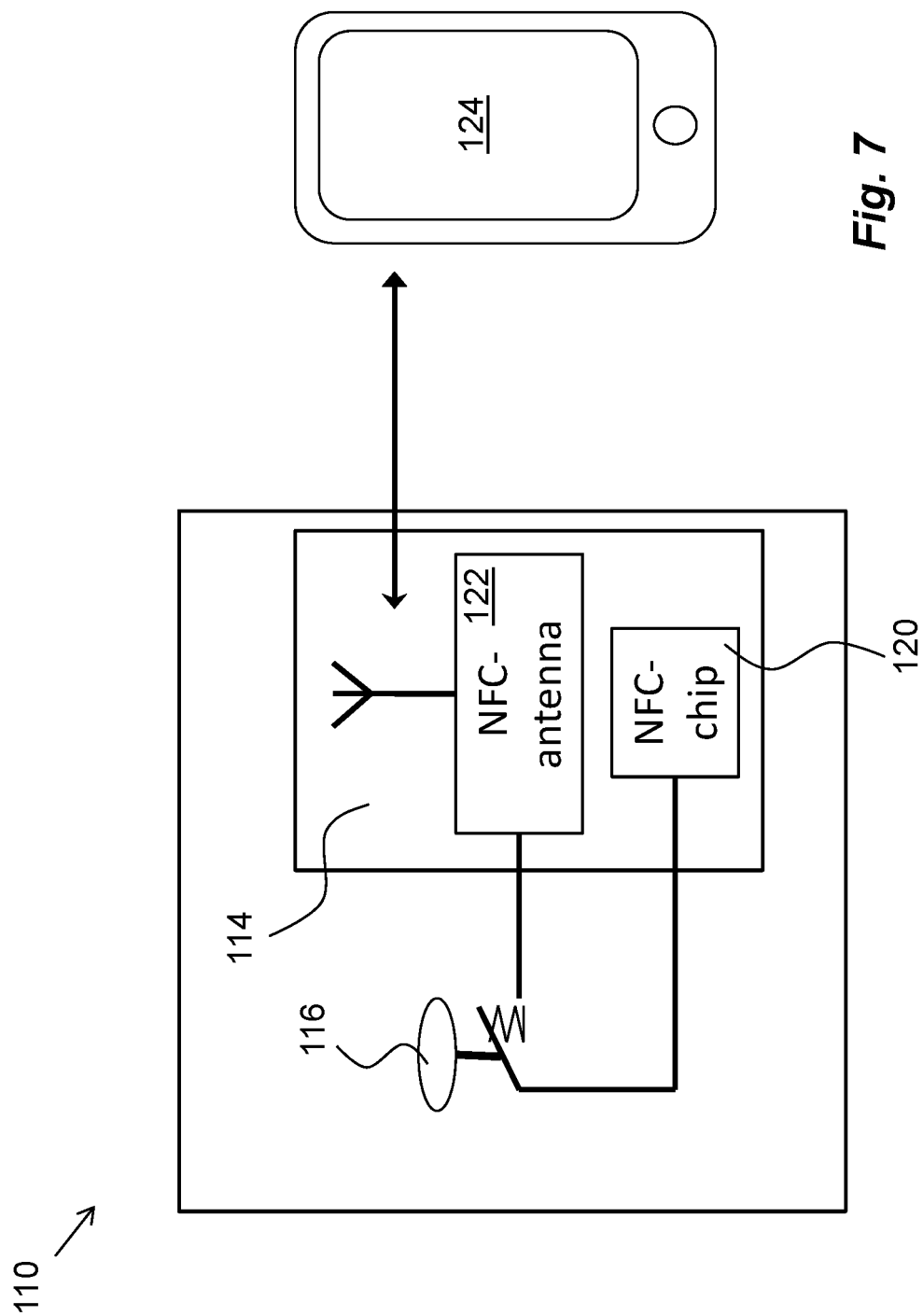

According to a solution shown schematically in FIG. 7, the information provider system 110 is arranged with one printed button area arranged as a switch 116 and intended to be touched or contacted by a user. When not activated, the switch is open. Further the switch 116 is placed between the antenna 122 and the NFC-chip 120 as seen in FIG. 7. Thus, even if a smart device 124 is placed on the marked area, the NFC-chip 120 is unaffected because the antenna 122 is disconnected. When the switch 116 is operated, the antenna 122 is connected to the NFC-chip 120, whereby the NFC-chip is energized by the connection between the antenna 122 and the smart device 124. The energizing of the NFC-chip 120 of the NFC-tag 114 causes the NFC-tag 114 to send a signal with specific information to the smart device 124 via the antenna 122. The specific information initiates a program in the smart device 124 to visually display various further information on its screen and/or to audibly present various further information via its loudspeaker. The further information is in this context related to the specific information from the NFC-tag. The further information is preferably also related to the printed visual information 112 on the information provider system 110. The further information may then be more detailed data, e.g. regarding the product that is displayed, a user manual of the product, safety and warranty documents etc.

As an example, the specific information from the NFC-tag 114 may trigger at least one step-by-step instruction program or application in the smart device, wherein the instruction is progressed each time the switch 116 is pressed. In this respect, the smart device is provided with a function that counts the number of times the switch is pressed. It is thereby feasible that when the last instruction step has been displayed on the smart device and the switch is pressed again, that the instruction re-starts with the first instruction step. The program(s) and/or application(s) may be stored in the smart device but may also be stored in external remote databases that are either retrieved by the smart device or run via web browsers. In that respect, the signal from the NFC-tag may activate the smart device to trigger a web browser to activate certain URL's. These may comprise e.g. instructions for use of the medicament delivery device, where the URL may lead to a web page containing a written description of how to use the device.

Figure 8:
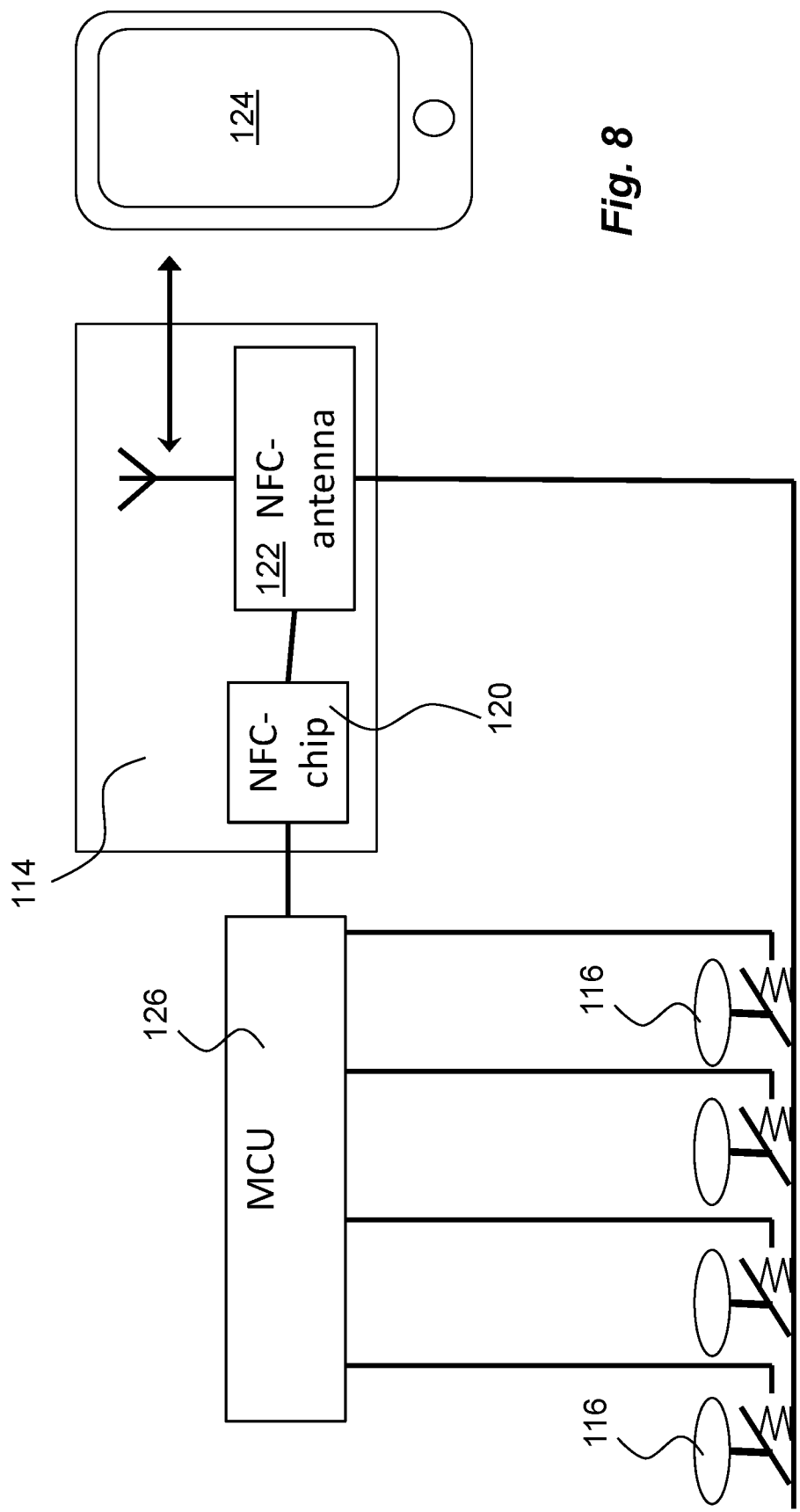

The concept can be developed to include other further information to the user by adding more switches. Preferably, a microcontroller unit 126 is included. See FIG. 8. With this solution a number of input channels may be used from a number of switches 116. The channels are connected to input gates of the micro controller. In this case the switches are not used for activating the NFC-tag 114. Instead, the NFC-tag 114 is activated when the smart device 124 is placed on the marked area. This is important because the micro-controller 126 requires power to function and the connection between the smart device 124 and the antenna 122 of the NFC-tag 114 provides energy harvesting from the smart device 124. Now the switches 116 are used as input signals to the microcontroller 126. Apart from the plurality of switches 116 providing activation of different functions, also certain predetermined combinations of active switches 116 may activate certain functions. Thus, with this solution, the possibilities are greater compared to the previously presented single-switch solution. For instance, more than one product, such as a medicament delivery device may be presented on the smart device, depending on which switch is activated. Also, different switches and/or combinations of switches may provide a choice of different languages that user instructions may be presented in. Further, switches may be used for answering quality of life questions, such as cognitive function, pain, fatigue, nausea, mental health, etc. These answers are then transmitted to the smart device via the NFC-tag, which in turn may be transmitted to dedicated receivers via suitable wireless networks that the smart device may communicate with.

A targeted web page may include a video recording of a narrator, showing and describing how to use the device. Further information that could be provided to the user is contact information to health care providers, such as telephone numbers, e-mail addresses, maps etc. Further information to a user may comprise reminders and schedules for dose delivery, such as dose delivery intervals, at what times during the day the dose should be taken etc.

The dose delivery information could be generated electronically from prescription, wherein the further information is obtained through communication with external remote databases via networks. The smart device could then provide the user with reminding information when it is time to take a dose of medicament, wherein the reminder could include all sorts of indications such as text messages on the display of the smart device, audible signals or voice messages, vibrations, flashes, just to mention a few possibilities.

Other types of further information could comprise reminders and schedules regarding using different dose delivery sites, which may be important when injection devices are used and wherein repeated injections on the same site may cause scarred tissue, and or where the drug injected may cause skin irritation. These schedules could comprise visual information on the display of the smart device showing graphically where on the body the next dose should be delivered. This type of further information may also be displayed in connection with the reminder of taking a dose of medicament.

Figure 9:
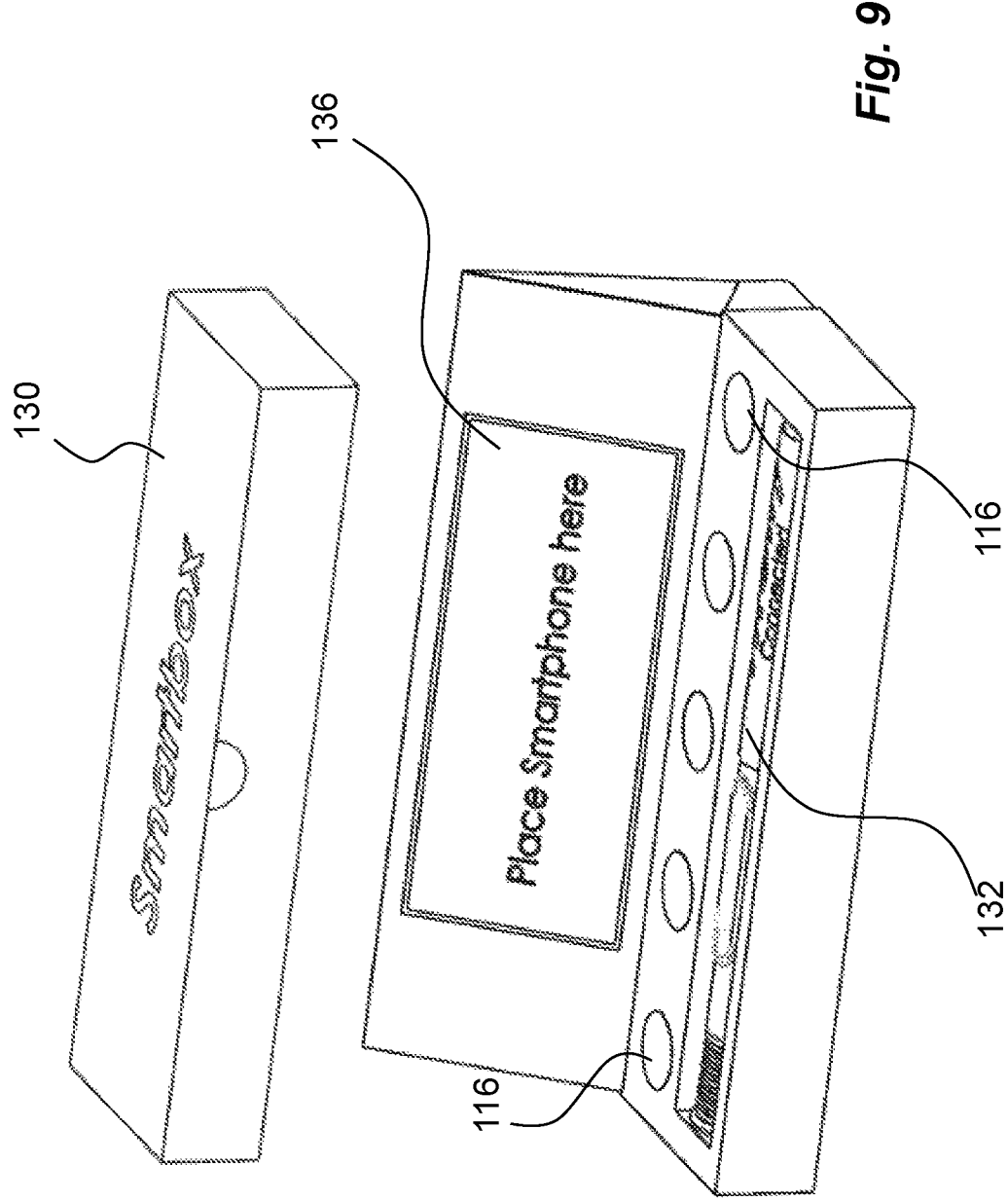
Figure 10:
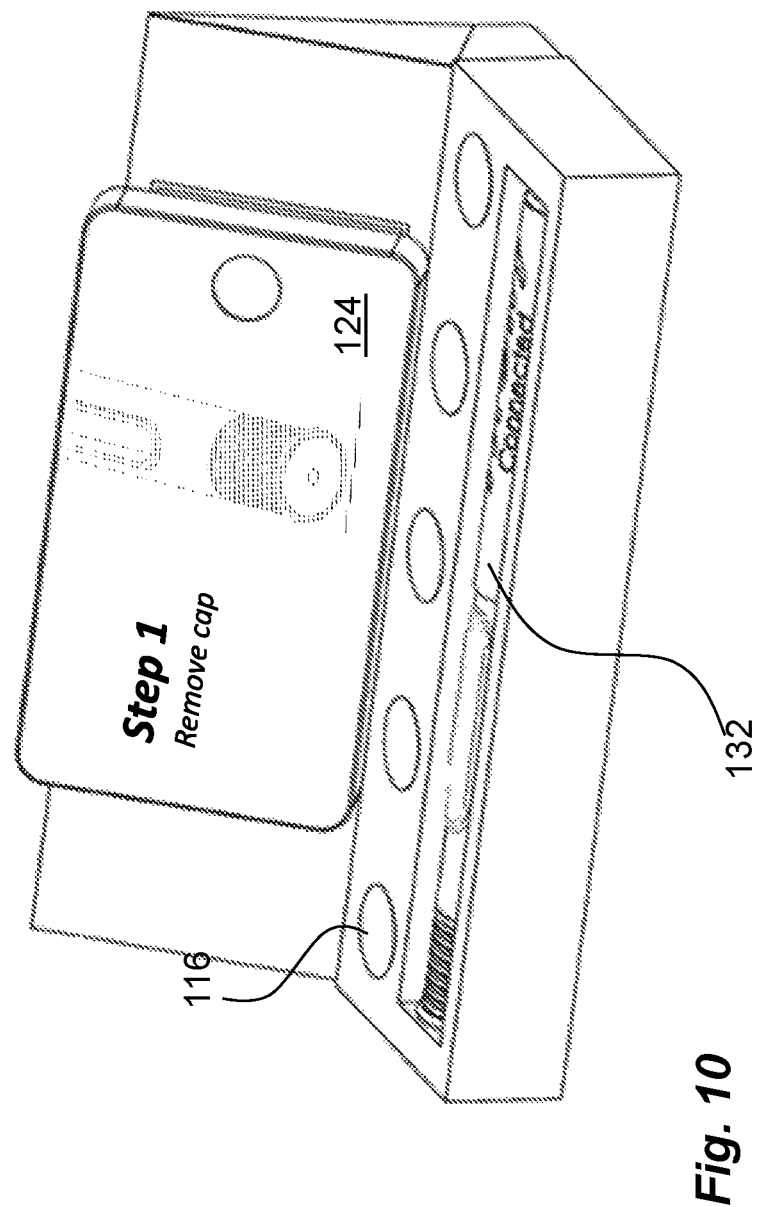

FIGS. 9 and 10 show the information provider system as a packaging 130 for a product 132, such as a medicament delivery device. In this context, the packaging of the medicament delivery device is arranged with an NFC-chip and with suitable circuitry as described above. The NFC-chip and the circuitry is preferably embedded in the packaging. A number of specific contact areas, e.g. printed button areas, that are intended to be touched or contacted by a user may be provided on the packaging, FIG. 9. Each specific contact area comprises a switch 116 under which the circuitry is placed so that touching or pressing the printed button areas will affect the switch 116 and thereby the circuitry so as to activate the NFC-chip to provide certain information. The packaging may further comprise a marked area 136 for placing the smart device 124, wherein the marked area is positioned in relation to the NFC antenna such that a good connection may be established.

When a smart device 124 is placed in the marked area of the packaging, the NFC-chip is energized by the smart device, FIG. 10. This could in turn cause an application to be installed in the smart device and started. Then, depending on which printed button area is pressed on the packaging, different further information is provided through the smart device. The further information could for instance include step-by-step instructions for use, and that could be displayed sequentially when pressing the printed button areas.

In addition to the medicament delivery devices described above, there might be further devices available to a user, or further functional features of the medicament delivery device, that could add to the functionality. For instance, additional sensors may be employed for measuring hard facts regarding the patient, where the information from the additional sensors are added to the patient history both regarding dose delivery adherence as well as health reports as established by questionnaires as mentioned above. The hard facts measured may come from blood samples, monitored heart rate, blood pressure measurements, saliva samples, just to mention a few.

It is to be understood that the embodiments described above and shown in the drawings are to be regarded only as non-limiting examples of the invention and that it may be modified in many ways within the scope of the patent protection.

The invention claimed is:

1. An information provider system for a medicament delivery device, the information provider system comprising:
   a sheet material operatively connected to the medicament delivery device and having printed information visible to a user regarding the medicament delivery device;
   at least one Near Field Communication (NFC)-tag imbedded in the sheet material and connected to circuitry, where the at least one NFC-tag is arranged with a chip containing specific information related to the medicament delivery device;
   an antenna imbedded in the sheet material and connected to the circuitry; and
   at least one touch switch imbedded in the sheet material and connected to the circuitry such that the antenna and NFC-tag are not in electrical communication when the touch switch is in an open position and when a user touches a specific area located on the sheet material the touch switch closes and the antenna and NFC-tag are electrically connected through the circuitry,
   wherein the specific information in the chip is not accessible or readable until the touch switch is closed,
   wherein closing of the touch switch connects the antenna to the NFC-tag, such that activation of an NFC-enabled smart device arranged adjacent the NFC-tag provides further information to a user based on the specific information contained within the NFC-tag.

2. The information provider system according to claim 1, wherein said further information regarding said specific information is stored in said smart device.

3. The information provider system according to claim 1, wherein said smart device is arranged with communication systems capable of communicating with remote databases, wherein said further information regarding said specific information is retrieved from said remote databases.

4. The information provider system according to claim 1, wherein said further information is provided visually and/or audibly.

5. The information provider system according to claim 1, wherein said at least one switch is positioned between said chip and said antenna, such that said antenna is connected to said chip when said at least one switch is operated.

6. The information provider system according to claim 1, wherein said smart device is arranged to register repeated operations of said at least one switch such that said smart device provides new further information to a user regarding said specific information each time said at least one switch is operated.

7. The information provider system according to claim 1, wherein it comprises a plurality of switches operably connected to said NFC-tag, and wherein said smart device is arranged to register operations of specific switches of the plurality of switches such that said smart device provides further information to a user regarding said specific information when a specific switch is operated.

8. The information provider system according to claim 7, wherein it further comprises a microcontroller operably connected between said plurality of switches and said NFC-tag, for handling a plurality of input signals from the plurality of switches.

9. The information provider system according to claim 1, wherein said sheet material comprises printed visual information of at least one product.

10. The information provider system according to claim 9, wherein said printed visual information on said sheet material comprises a plurality of products, wherein said plurality of switches are associated with said plurality of products.

11. The information provider system according to claim 1, wherein the sheet material comprises a packaging for a product and wherein the printed visual information presented on said packaging and the specific information of the chip is related to said product.

12. The information provider system according to claim 11, wherein said product to be contained in said packaging is a medicament delivery device.

13. The information provider system according to claim 12, wherein said further information provided to a user by said smart device comprises user instructions for said medicament delivery device, and/or information about a medicament of the medicament delivery device.

14. The information provider system according to claim 13, wherein said user instructions are designed as step-by-step handling instructions that are progressed each time a switch is operated.

15. The information provider system according to claim 13 further comprising a plurality of switches operably connected to said NFC-tag,
wherein said smart device is arranged to register operations of specific switches of the plurality of switches such that said smart device provides further information to a user regarding said specific information when a specific switch is operated and,
wherein said user instructions are changed when one of said plurality of switches is operated or when predetermined combinations of switches are operated.

16. The information provider system of claim 1 further comprising a medicament delivery device.

17. An information provider system for a medicament delivery device, said information provider system comprising:
a smart device that is Near Field Communication (NFC) enabled;
a sheet material operatively connected to the medicament delivery device and having printed information visible to a user regarding the medicament delivery device;
at least one NFC-tag is arranged to said sheet material and connected to circuitry, where said at least one NFC-tag is arranged with a chip containing specific information related to the medicament delivery device;
an antenna arranged to the sheet material and connected to the circuitry, where the NFC-tag is activated when the smart device is placed in a marked area positioned in relation to the antenna such that a connection is established between the smart device and the antenna; and
a plurality of switches operably connected to a microcontroller unit that is operatively connected to said NFC-tag such that the activation of the NFC-tag provides energy from the smart device to the microcontroller through the circuitry;
wherein the specific information in the chip is not accessible or readable until the NFC-tag is activated,
wherein activation of any one of the plurality of switches connects the microcontroller to the activated NFC-tag, such that the smart device can receive the specific information contained in the chip.

18. The information provider system of claim 17, whereby said smart device provides further information to a user regarding the specific information of the NFC-tag.

19. The information provider system according to claim 18, wherein said further information provided to a user by said smart device comprises user instructions for said medicament delivery device, and/or information about a medicament of the medicament delivery device.

20. The information provider system of claim 17, wherein the sheet material comprises a packaging for a product and wherein the printed visual information presented on said packaging and the specific information of the chip is related to said product.

21. The information provider system according to claim 1, wherein the at least one touch switch and the antenna are imbedded in the sheet material.

* * * * *